United States Patent [19]

Klaumünzner et al.

[11] Patent Number: 5,107,055
[45] Date of Patent: Apr. 21, 1992

[54] METHOD FOR SIMULTANEOUS RECOVERY OF PURE BENZENE AND PURE TOLUENE

[75] Inventors: Udo Klaumünzner, Mülheim/Ruhr; Hans-Jürgen Vollmer, Essen, both of Fed. Rep. of Germany

[73] Assignee: Krupp Koppers GmbH, Essen, Fed. Rep. of Germany

[21] Appl. No.: 624,325

[22] Filed: Dec. 5, 1990

[30] Foreign Application Priority Data

Dec. 23, 1989 [DE] Fed. Rep. of Germany ....... 3942950

[51] Int. Cl.$^5$ .......................... C07C 7/00; C07C 7/10
[52] U.S. Cl. .................... 585/808; 585/834; 585/863; 585/865; 208/58; 208/81; 208/82
[58] Field of Search ............ 585/808, 834, 863; 208/865, 58, 81, 82, DIG. 6

[56] References Cited

U.S. PATENT DOCUMENTS

| 4,586,986 | 5/1986 | Preusser et al. | 585/808 |
| 4,725,338 | 2/1988 | Asanuma et al. | 203/DIG. 6 |
| 4,925,535 | 5/1990 | Preusser et al. | 585/808 |

*Primary Examiner*—Anthony McFarlane
*Assistant Examiner*—Nhat Phan
*Attorney, Agent, or Firm*—Michael J. Striker

[57] ABSTRACT

A simultaneous recovery of pure benzene and pure toluene is performed by extractive distillation with N-formylmorpholine and/or other N-substituted morpholines whose substituents contain not more than seven C-atoms as a solvent. From the entry product by predistillation, a benzene fraction boiling in the region between 75° and 85° C. and a toluene fraction boiling in the region between 99° and 111° C. is separated. The benzene fraction is supplied in the lower part, and the toluene fraction is supplied in the upper part of the extractive distillation column separated by a chimney plate into two parts.

6 Claims, 2 Drawing Sheets

METHOD FOR SIMULTANEOUS RECOVERY OF PURE BENZENE AND PURE TOLUENE

BACKGROUND OF THE INVENTION

The present invention relates to a method for simultaneous recovery of pure benzene and pure toluene from hydrocarbon mixtures which contain these aromates.

More particularly, it relates to such a method in which the recovery is performed by extractive distillation with N-formylmorpholine and/or other N-substituted morpholines, whose substitutes contain not more than seven C-atoms as selective solvent. The entry product prior to introduction into the extractive distillation column is subjected to a predistillation, in which the ingredients which boil higher than the above mentioned aromates are separated as sump product.

The separation of aromates from hydrocarbon mixtures by extractive distillation with the above mentioned N-substituted morpholine as selective solvent is known for a long time. It is disclosed for example in the German patent 1,568,940. With the utilization of N-formylmorpholine as selective solvent, the above described method have grown in numerous method production installations. When the entry product, in addition to benzene, also has high quantities of toluene as well as in some cases xylene, it is not advisable to subject this entry product directly to an extractive distillation. Due to the high boiling point of the toluene and the xylene, in this case the sump temperature in the extractive distillation column must be raised so that in the boiling region of these aromates also boiling non-aromates are completely evaporated from the sump of the extractive distillation. This increase of the sump temperature has the result that depending on the height of the temperature a high or average quantity of benzene escapes together with the non-aromates and the vapor through the head from the extractive distillation column. Thereby the benzene yield is correspondingly low.

In order to avoid this it is proposed in the German document DE-OS 1,543,119 to use a specific solvent without bond which, for the introduction of the entry product into the extractive distillation column, subjects the entry product to a predistillation in a manner that the components boiling higher than the aromates recovered are separated as sump products, while the precipitated aromate-containing head product is supplied without further separation into the extractive distillation column. In other words, in this method, depending upon the entry product and the method either benzene and toluene or benzene, toluene and xylene together with the corresponding boiling non-aromates are supplied into the extractive distillation columns.

This procedure which in practice is used with the above mentioned solvent, leads to the simultaneous recovery of benzene and toluene from a head product which contains these components. However, the extractive distillation column delivers a highly pure benzene. The non-aromate content of the recovered toluene lies however partially at approximately 1.5 weight percent. Since for predetermined applications a higher purity of the toluene is needed, these results are satisfactory only partially.

SUMMARY OF THE INVENTION

Accordingly, it is an object of the present invention to provide a method of the above mentioned general type, which eliminates the disadvantages of the prior art.

More particularly, it is an object of the present invention to provide a method of the above mentioned type in which the purity of the recovered toluene is increased without a traceable increase in installation and operational costs.

In keeping with these objects and with others which will become apparent hereinafter, one feature of the present invention resides, briefly stated, in a method in accordance with which for an extractive distillation, a column is utilized which is separated by a chimney plate arranged in a central region into an upper part and a lower part, the entry product during a predistillation is separated into a benzene fraction boiling in the region between 75° and 85° C. and a toluene fraction boiling in the region between 99° and 111° C., the benzene fraction is supplied in the center of the lower part, the toluene fraction is supplied in the center of the upper part, and the solvent is supplied in two partial streams to the head of the column and also immediately under the chimney plate into extractive distillation columns.

In other words, the method is performed in reverse to the known methods in which the benzene and toluene together are withdrawn as head products from the predistillation and supplied into the extractive distillation column first in the predistillation and separation into a benzene and toluene fraction is performed and they are separately supplied at different locations into the extractive distillation column. For this purpose the extractive distillation column is separated by a chimney plate arranged in its central region into an upper part and a lower part, which are provided at their upper ends with connections for feeding of the solvent.

Advantageously, the upper part of the extractive distillation column has an additional device for the heat supply, for example in the form of a circulating boiler arranged at the height of the chimney plate on the extractive distillation column. A part of the liquid collected on the chimney plate is supplied through the circulating boiler and heated in it.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
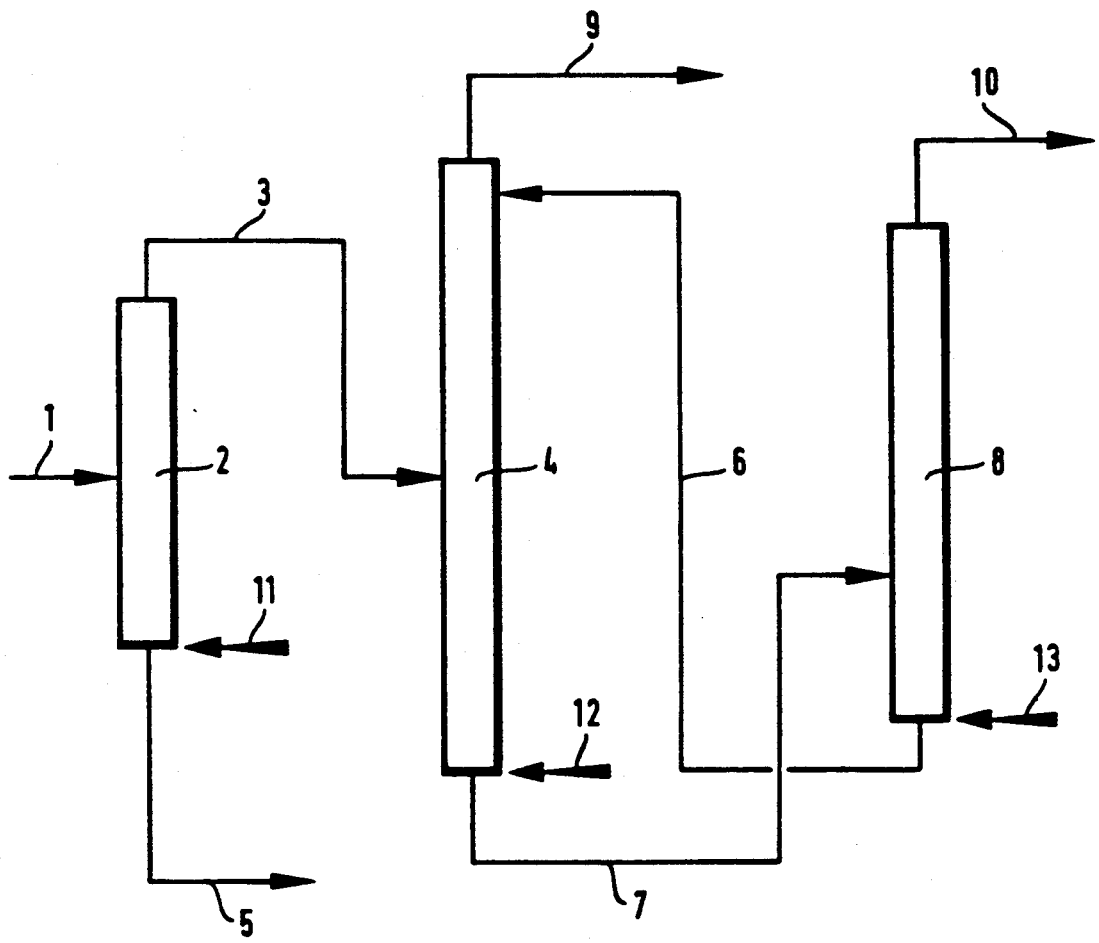
FIG. 1 is a flow diagram of a conventional method for recovery of pure benzene and pure toluene.

The flow diagrams show only those devices which are important for understanding of the new method in accordance with the present invention. Such auxiliary devices as a circulating boiler, heat exchanger, valves and pumps as well as devices for solvent regeneration are not shown in the drawings.

As can be seen from the flow diagram of FIG. 1, the entry product is supplied through a conduit 1 into a predistillation column 2. The entry product can be any hydrocarbon which contains differing benzene, toluene and xylene for example brick oven benzene-pressure raffinate, pyrolysis benzene or reformate benzene. In the predistillation column provided with plates or similar inserts, the benzene and the toluene together with the corresponding boiling non-aromates are distillated through the head and supplied via a conduit 3 into the central part of the extractive distillation column 4. The higher boiling hydrocarbons are withdrawn as sump product through a conduit 5 from the predistillation column 2.

In an extractive distillation column 4 which can also be provided with plates or similar inserts, the separation of the non-aromates from aromates is performed. The required solvent (for example N-formylmorpholine) is supplied through a conduit 6 at the head to the extractive distillation column 4. The aromates together with the solvent are withdrawn as extract from the sump of the extractive distillation column and supplied through a conduit 7 into a stripping column 8. Simultaneously the non-aromates escape in the form of vapor through the head from the extractive distillation column 4 and supplied through a conduit 9 to a further treatment. In the stripping column 8 the separation of the aromates from the solvent is performed. The aromates are withdrawn as head product through a conduit 10 from the stripping column 8 and finally are distillatively separated in a not shown column. The solvent purified from the aromates is removed from the sump of the stripping column 8 and supplied through the conduit 6 for further use to the extractive distillation column 4. The arrows 11, 12 and 13 illustrate the heat supplied to the individual columns, which can be performed for example through a correspondingly arranged circulating boiler.

It can be understood from the above that the above specified operation leads to a benzene with a very high purity, while the purity of the recovered toluene is not sufficient for some applications. Since a post-cleaning of the toluene recovered in this manner is not possible from economic reasons, the method has a disadvantage which is eliminated in the inventive method illustrated in FIG. 2.

Figure 2:
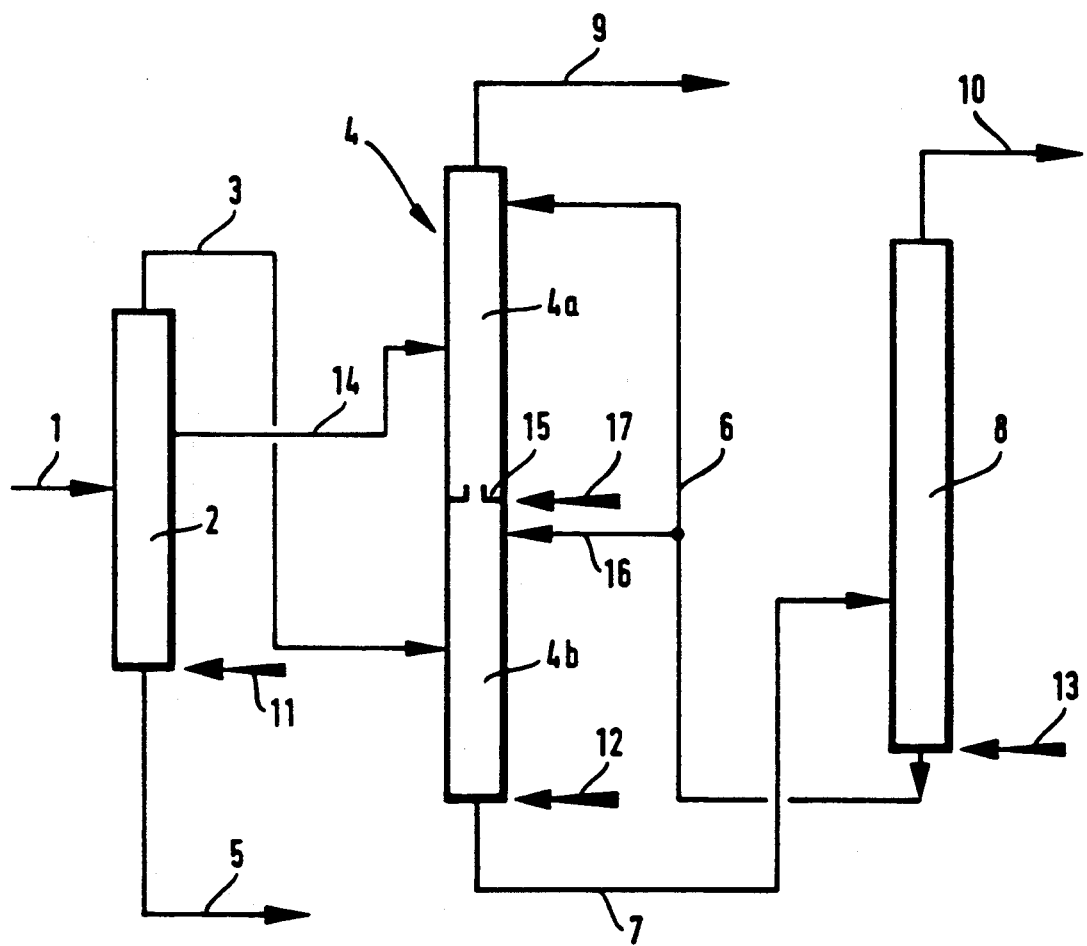
FIG. 2 is a flow diagram of the method for recovery of pure benzene and pure toluene in accordance with the present invention.

The installation shown in FIG. 2 substantially corresponds to the installation shown in FIG. 1, and parts of the installation of FIG. 2 which corresponds to the parts of FIG. 1 are identified with the same reference numerals. The predistillation column 2 operates with such conditions that through the head only the benzene fraction boiling in the region between 75° and 87° C. is withdrawn through the conduit 3, and the toluene fraction boiling in the region between 99° and 111° C. is withdrawn through the conduit 14 as a side stream. The higher boiling components of the entry product are removed conventionally through the conduit 5 from the sump of the predistillation column 2. The extractive distillation column 4 in this case is subdivided by a chimney plate located in the central region of the column into an upper part 4a and a lower part 4b. In a column with a total 94 theoretical plates, the chimney plate 15 can be arranged at the height of the 53rd plate from above. The benzene fraction withdrawn through the conduit 3 is supplied into the extractive distillation column in the middle of the lower part 4b while the toluene fraction withdrawn through the conduit 14 is supplied through the center of the upper part 4a into the extractive distillation column. In the above mentioned column the inlet for the toluene fraction is located for example at the height of the 30th bottom plate from above, and the inlet for the benzene fraction is located at the height of 77th bottom plate from above. An additional heat supply is provided in this case for the upper part 4a as identified with the arrow 17. For this purpose a circulating boiler can be used for example at the height of the chimney plate 15. In principle the operation of the extractive distillation column 4 corresponds to the conventional diagram. In other words, the non-aromates are withdrawn as raffinates through the head via the conduit 9, and the aromates together with the solvent are withdrawn as extract from the sump of the extractive distillation column 4 and supplied through the conduit 7 into the stripping column 8. The conventional stripping of the aromates from the solvent is performed in the stripping column 8. A partial stream is branched through the conduit 16 from the solvent withdrawn from the conduit 6 and supplied into the lower part 4b closely under the chimney plate 15. The remaining solvent is supplied through the conduit 6 to be fed into the extractive distillation column 4. With the above mentioned column with 94 theoretical plates, the inlet for the conduit 6 is located for example at the height of the first plate from above, and the inlet for the conduit 16 is located at the height of 54th plate from above. The separation of the solvent is performed in such a manner that the partial streams are equivalent to the respective entry product quantities. The inventive method operates with a ratio between the end product and the solvent in the region of between 1:3 and 1:6. The separation of the aromate withdrawn through the conduit 10 leads to a toluene with a purity which is substantially better than in the case of utilization of the method in accordance with the prior art.

This is confirmed by the following comparative test, in which the inventive method shown in FIG. 2 is compared with the method in accordance with the prior art shown in FIG. 1. Starting from the same entry product and the same entry product quantity as well as the same ratio of the entry product to the solvent (N-formylmorpholine) of 1:4.3, the test results are presented in the following table:

|  |  | Invention FIG. 2 | Prior Art Technique FIG. 1 |
| --- | --- | --- | --- |
| Head product conduit 9 | (kg/h) | 9 342 | 9.109 |
| Benzene in head product | (%) | 4.81 | 12.32 |
|  | (kg/h) | 449 | 1 123 |
| Toluene in head product | (%) | 5.78 | 1.73 |
|  | (kg/h) | 540 | 158 |
| Benzene yield | (%) | 94.48 | 96.19 |
| Toluene yield | (%) | 98.33 | 49.51 |
| Non-aromates in benzene | (ppm) | 931 | 4 |
| Non-aromates in toluene | (ppm) | 2 020 | 18.130 |
| Heat quantity | (MW) | 20.05 | 20.05 |

As can be seen from the comparative test, the use of the inventive improves the purity of the recovered toluene considerably. While in the comparative test the purity of the recovered benzene with the use of the inventive method is somewhat lower than with the use of the known method, the benzene yield is however higher. If the process conditions in the inventive method are however adjusted so that the benzene yield is correspondingly reduced, the similarly high benzene units are obtained as in the method in accordance with the prior art. Since the energy consumption in both methods is equal, the objectives of the invention are believed to be completely achieved. A comparison of the flow diagrams of FIGS. 1 and 2 show moreover that the inventive method needs only small modifications in the installation of FIG. 1. The inventive method is suitable for converting the existing installations without significant investment costs.

It should also be mentioned that the predistillation of the entry product can be performed in two columns instead of one column when it is desirable in view of the operational conditions.

It will be understood that each of the elements described above, or two or more together, may also find a useful application in other types of methods differing from the types described above.

While the invention has been illustrated and described as embodied in a method for simultaneous recovery of pure benzene and pure toluene, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A method for simultaneous recovery of pure benzene and pure toluene from an entry product containing hydrocarbons including the benzene and toluene, comprising the steps of:
    a. predistilling the entry product to separate ingredients of the entry product boiling at a higher temperature than the benzene and toluene and to form a toluene fraction boiling in a range between 99° and 111° C. and a benzene fraction boiling in a range between 75° and 85°, said toluene fraction being separate from said benzene fraction;
    b. performing an extractive distillation of said benzene fraction and said toluene fraction with an N-substituted morpholine whose substituents contain not more than seven C-atoms as selective solvent into an extractive distillation column divided into an upper part and a lower part by a chimney plate, said chimney plate being located in the vicinity of a center of said distillation column;
    c. feeding the benzene fraction into said extractive distillation column in a center of the lower part of the extractive distillation column;
    d. feeding the toluene fraction into said extractive distillation column in a center of the upper part of the extractive distillation column;
    e. feeding one stream of the solvent into the extractive distillation column at the head of the extractive distillation column; and
    f. feeding another stream of the solvent into the extractive distillation column closely under the chimney plate.

2. A method as defined in claim 1, wherein the N-substituted morpholine is N-formylmorpholine.

3. A method as defined in claim 1, and further comprising the steps of supplying heat required for the extractive distillation both in the lower part and in the upper part of the extractive distillation column.

4. A method as defined in claim 1, wherein said extractive distillation is performed with a ratio of the entry product to the solvent between 1:3 and 1:6.

5. A method for simultaneous recovery of pure benzene and pure toluene from an entry product containing hydrocarbons including the benzene and toluene, comprising the steps of:
    a. predistilling the entry product to separate ingredients of the entry product boiling at a higher temperature than the benzene and toluene and to form a toluene fraction boiling in a range between 99° and 111° C. and a benzene fraction boiling in a range between 75° and 85°, said toluene fraction being separate from said benzene fraction;
    b. performing an extractive distillation of said benzene fraction and said toluene fraction with an N-substituted morpholine whose substituents contain not more than seven C-atoms as selective solvent with a ratio of the entry product to the solvent in a range of from 1:3 to 1:6, said extractive distillation being performed in an extractive distillation column divided into an upper part and a lower part by a chimney plate;
    c. feeding the benzene fraction into said extractive distillation column in the vicinity of a center of the lower part of the extractive distillation column;
    d. feeding the toluene fraction into said extractive distillation column in the vicinity of a center of the upper part of the extractive distillation column;
    e. feeding one stream of the solvent into the extractive distillation column at the head of the extractive distillation column;
    f. feeding another stream of the solvent into the extractive distillation column closely under the chimney plate; and
    g. supplying heat for the extractive distillation both to the lower part of the extractive distillation column and the upper part of the extractive distillation column.

6. A method as defined in claim 5, wherein the N-substitute morpholine is N-formylmorpholine.

* * * * *